United States Patent [19]

Augstein et al.

[11] 4,006,245
[45] Feb. 1, 1977

[54] CHEMICAL COMPOUNDS

[75] Inventors: Joachim Augstein, Linford; David Carter; Thomas Brian Lee, both of Loughborough, all of England

[73] Assignee: Fisons Limited, England

[22] Filed: Jan. 29, 1975

[21] Appl. No.: 545,309

Related U.S. Application Data

[62] Division of Ser. No. 276,798, July 31, 1972, Pat. No. 3,882,148.

[30] Foreign Application Priority Data

July 29, 1971 United Kingdom ............ 35605/71

[52] U.S. Cl. .................................. 424/283; 424/269
[51] Int. Cl.² ....................................... A61K 31/35
[58] Field of Search ................. 424/283; 260/345.2

[56] References Cited
UNITED STATES PATENTS

| | | | |
|---|---|---|---|
| 3,419,578 | 12/1968 | Fitzmaurice et al. | 424/283 |
| 3,671,625 | 6/1972 | Altounyan | 424/283 |
| 3,823,165 | 7/1974 | Cairns et al. | 424/283 X |

Primary Examiner—Frederick E. Waddell
Attorney, Agent, or Firm—Wenderoth, Lind & Ponack

[57] ABSTRACT

There are provided compounds of formula I,

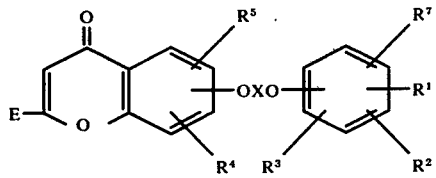

wherein
$R^1$, $R^2$, $R^3$, $R^4$, $R^5$ and $R^7$ may be the same or different, and are hydrogen, hydroxy, alkoxy, alkoxy substituted by phenyl, acyl, amino, acylamino, alkenyl, halogen, or alkyl, provided that at least one of $R^1$, $R^2$, $R^3$ and $R^7$ are other than hydrogen and hydroxy,
or an adjacent pair of $R^1$, $R^2$, $R^3$ and $R^7$ represent a chain —COCH=CH—O—,
X is a hydrocarbon chain containing from 2 to 10 carbon atoms and optionally substituted by a hydroxy group, and
E is a carboxy group or a tetrazole group,
and pharmaceutically acceptable derivatives thereof.

The compounds are indicated for use as antagonists of SRS-A.

1 Claim, No Drawings

CHEMICAL COMPOUNDS

This is a division of application Ser. No. 276,798, filed July 31, 1972, now U.S. Pat. No. 3,882,148.

This invention relates to new compounds, methods for their preparation and compositions containing them.

According to our invention we provide compounds of formula

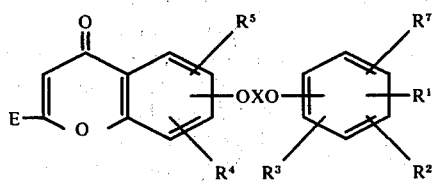

wherein
$R^1$, $R^2$, $R^3$, $R^4$, $R^5$, and $R^7$ may be the same or different, and are hydrogen, hydroxy, alkoxy, alkoxy substituted by phenyl, acyl, amino, acylamino, alkenyl, halogen, or alkyl, provided that at least one of $R^1$, $R^2$, $R^3$ and $R^7$ are other than hydrogen and hydroxy,
or an adjacent pair of $R^1$, $R^2$, $R^3$ and $R^7$ represent a chain —COCH=CH—O—,
X is a hydrocarbon chain containing from 2 to 10 carbon atoms and optionally substituted by a hydroxy group, and
E is a carboxy group or a tetrazole group,
and pharmaceutically acceptable derivatives thereof.

According to our invention we also provide a process for the production of a compound of formula I, or a pharmaceutically acceptable derivative thereof, which comprises,
a. producing a compound of formula Ia,

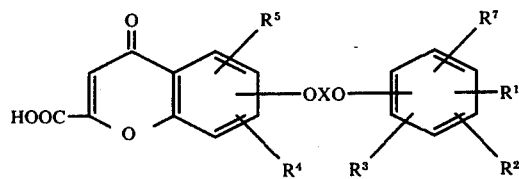

in which
$R^1$, $R^2$, $R^3$, $R^4$, $R^5$, $R^7$ and X are as defined above, by cyclising a compound of formula II,

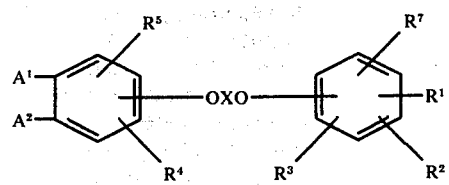

wherein
$R^1$, $R^2$, $R^3$, $R^4$, $R^5$, $R^7$ and X are as defined above, and
$A^1$ and $A^2$ are the pairs of groups
i. —OH and —COCH$_2$COCOR$^6$, or
ii. —O—C(COOM)=CH—COOM and —H
in which
$R^6$ is an —OM group or a group hydrolysable thereto, and M is hydrogen or an alkali metal,
b. reacting a compound of formula III,

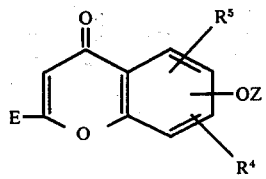

or an ester thereof,
in which
$R^4$, $R^5$ and E are as defined above, and
Z is hydrogen or a reactive metal, or a hydrocarbon chain containing from 2 to 10 carbon atoms and carrying an anion forming group or an epoxide group,
with a compound of formula IV,

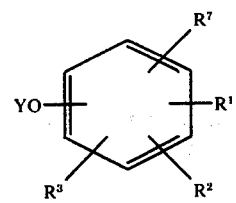

wherein
$R^1$, $R^2$, $R^3$ and $R^7$ are as defined above, and
Y represents hydrogen or a reactive metal when Z represents a hydrocarbon chain containing from 2 to 10 carbon atoms carrying an anion forming group or an epoxide group, and, when Z represents hydrogen or a reactive metal, Y represents a hydrocarbon chain containing from 2 to 10 carbon atoms and carrying an anion forming group or an epoxide group,
c. producing a compound of formula Ia by hydrolysing a compound of formula XIII,

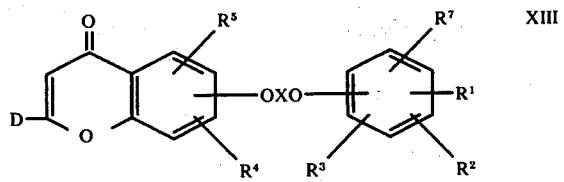

in which
$R^1$, $R^2$, $R^3$, $R^4$, $R^5$, $R^7$ and X are as defined above, and
D represents a group hydrolysable to a —COOH group,
d. producing a compound of formula Ib,

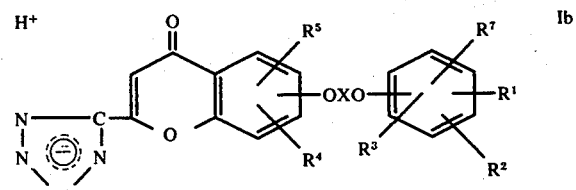

in which
$R^1$, $R^2$, $R^3$, $R^4$, $R^5$, $R^7$ and X are as defined above, by reacting a compound of formula XIV,

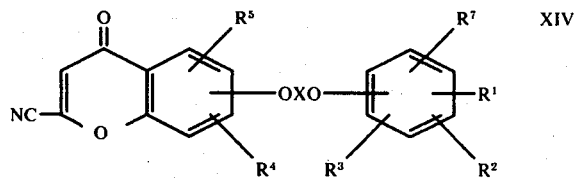

in which
R¹, R², R³, R⁴, R⁵, R⁷ and X are as defined above, with an azide in a solvent which is inert under the reaction conditions, e. producing a compound of formula Ic,

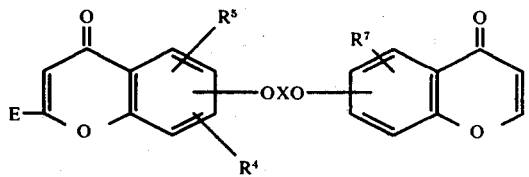

in which
R⁴, R⁵, R⁷, X and E are as defined above by cyclising a compound of formula XVI,

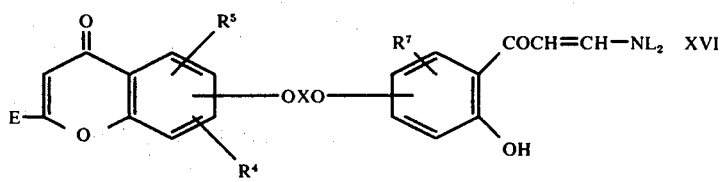

in which
R⁴, R⁵, R⁷, X and E are as defined above, and
L is an alkyl group, or f. producing a compound of formula Id,

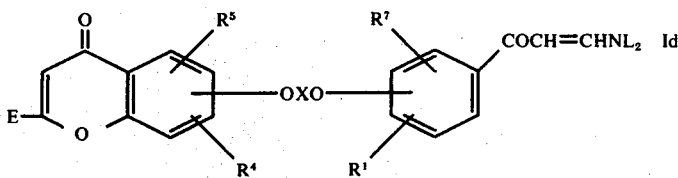

in which
R¹, R⁴, R⁵, R⁷, X, L and E are as defined above, by reacting a compound of formula XVII,

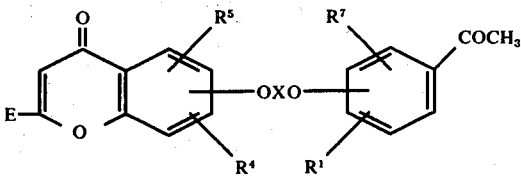

in which
R¹, R⁴, R⁵, R⁷, X and E are as defined above, with a compound of formula XVIII,

  XVIII or an acetal thereof, in which L is as defined above, and where desired or necessary converting the resulting compound of formula I to a pharmaceutically acceptable derivative thereof or vice versa.

The cyclisation of process (a) (i) may be carried out by heating, or under basic or neutral conditions. It is however preferred to carry out the cyclisation in the presence of an acid, e.g. hydrochloric acid, and in a solvent which is inert under the reaction conditions. The reaction may be carried out at from about 20° to 150° C. The group —OOR⁶ is preferably an ester group in which, for example R⁶ is a lower alkanol group.

The cyclisation of process (a) (ii) may be carried out by treating the compound of formula II with a cyclising agent, for example a dehydrating agent such as polyphosphoric, chlorosulphonic or sulphuric acid.

The reaction is preferably carried out under anhydrous conditions. Alternatively cyclisation may be achieved by converting the free carboxy groups of the compound of formula II to acyl halide groups and subjecting the resulting acyl halide to an intramolecular Friedel-Crafts reaction.

Process (a) (i) is in particular useful when R¹, R², R³ and R⁷ do not include an —OH group and a —COCH₃ in adjacent positions. Process (a) (ii) is in particular useful when R¹, R², R³ and R⁷ do not include a —OH group and hydrogen in adjacent positions.

In process (b) when Y or Z is a reactive metal the metal may be, for example, an alkali metal, e.g. sodium or another reactive metal, e.g. thallium. When Y or Z represent a hydrocarbon chain carrying an anion forming group the anion forming group may be, for example, a halogen atom, e.g. bromine, or a sulphonate group, e.g. a methyl sulphonate or a p-toluenesulphonate group. When Y or Z represents a hydrocarbon chain carrying a halogen atom the reaction may be carried out in the presence of a solvent which is inert under the reaction conditions, e.g. acetone and in the presence of an acid acceptor, e.g. potassium carbonate. The reaction is also preferably carried out under anhydrous conditions and in the presence of a suitable catalyst, e.g. KI. When Y or Z represent a hydrocarbon group carrying an epoxide the reaction may be carried out at an elevated temperature in a solvent which is inert under the reaction conditions, e.g. dioxan or dimethylformamide, and in the presence of a suitable catalyst, e.g. trimethylbenzylammonium hydroxide.

In process (c) the group D may be, for example, an ester, amide or nitrile group, which may be hydrolyzed to a —OOOH group. The hydrolysis may be carried out using conventional techniques, for example, under mildly basic conditions, e.g. using sodium bicarbonate.

Suitable solvents which are inert under the reaction conditions of process (d) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono- di- tri- and tetra-methylammonium, anilinium, morpholinium and piperidinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above the reaction may be carried out using hydrazoic acid (hydrogen azide) at a temperature of from about 20° to 160° C in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid. Process (d) is believed to pass through a compound of formula XV,

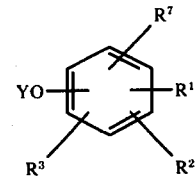

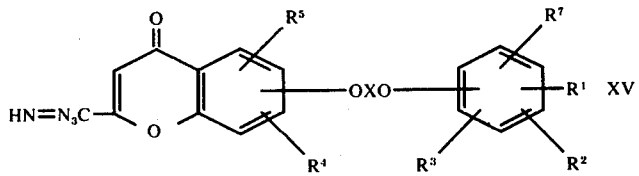

in which
$R^1$, $R^2$, $R^3$, $R^4$, $R^5$, $R^7$ and X are as defined above. The cyclisation of process (e) may be carried out under the same conditions as process (a) (i).

In process (f) it is preferable to use an acetal of the compound of formula XVIII, for example a di-alkyl acetal, e.g. a dimethyl acetal. The reaction may conveniently be carried out at an elevated temperature, e.g. from about 100° to 200° C, in a solvent which is inert under the reaction conditions, e.g. xylene.

Compounds of formula II may be made by reacting a compound of formula V,

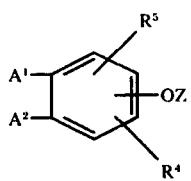

in which $A^1$, $A^2$, $R^4$, $R^5$ and Z are as defined above, with a compound of formula VI,

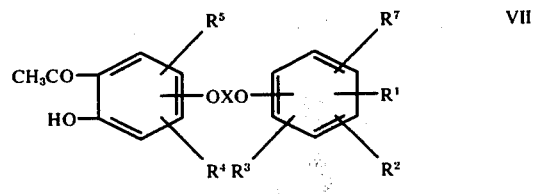

in which
$R^1$, $R^2$, $R^3$, $R^7$ and Y are as defined above, under the conditions of process (b).

Compounds of formula II in which $A^1$ and $A^2$ are the pair of groups —OH and —COCH$_2$COCOR$^6$, and in particular those compounds in which an adjacent pair of $R^1$, $R^2$, $R^3$ and $R^7$ are not an —OH group and a —COCH$_3$ group, may also be made by reacting a compound of formula VII,

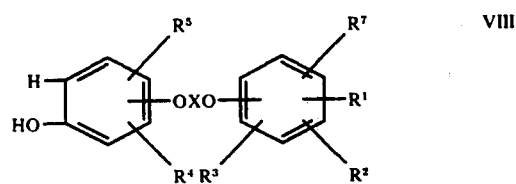

in which
$R^1$, $R^2$, $R^3$, $R^4$, $R^5$, $R^7$ and X are as defined above, with a dialkyl oxalate, e.g. diethyl oxalate in manner known per se.

Compounds of formula II in which $A^1$ and $A^2$ are the pair of groups —O—C(COOM)=CH—COOM and —H and in particular those compounds in which an adjacent pair of $R^1$, $R^2$, $R^3$ and $R^7$ are not an —OH group and hydrogen, may be made by reacting a compound of formula VIII,

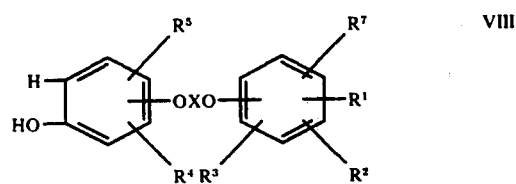

in which
$R^1$, $R^2$, $R^3$, $R^4$, $R^5$, $R^7$ and X are as defined above, with acetylene dicarboxylic acid or an ester thereof in manner known per se.

Compounds of formula VII and VIII may be made by linking a compound of formula IX or X,

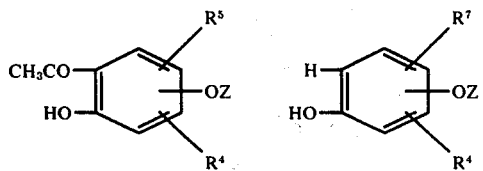

respectively, with a compound of formula XI,

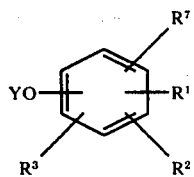

in which formulae $R^1$, $R^2$, $R^3$, $R^4$, $R^5$, $R^7$, Z and Y are as defined above, using the same techniques as in process (b) above.

Compounds of formula XIV may be made by dehydrating the corresponding 2-carboxyamide using, for example, phosphorous oxychloride, as dehydrating agent. The reaction is preferably carried out using at least one molar equivalent of dehydrating agent per mole of carboxyamide. Where the dehydrating agent reacts with one of $R^1$, $R^2$, $R^3$, $R^4$, $R^5$, $R^7$ or X (e.g. a substituent comprising an —OH group) sufficient dehydrating agent should be used to satisfy the side reaction as well as the main reaction. The reaction may, if desired, be carried out in the presence of an acid binding agent, e.g. triethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C depending on the dehydrating agent used. When phosphorus oxychloride is used a temperature of from 0° to 100° C is preferred.

The 2-carboxyamides may be made in manner known per se by reacting the corresponding 2-carboxylic acid esters with ammonia, e.g. using an alkanol as a solvent at a temperature of 0° to 120° C.

The compounds of formulae V, VI, XI, X and XVIII are either known or may be made from known starting materials in a manner known for the production of similar known compounds. Compounds of formula XVI may be made by process (i) above and compounds of formula XVII may be made by any one of processes (a), (b) or (c) above.

The compounds of formula I, and where desired or necessary, the intermediates therefor, may be recovered from the reaction mixtures in which they are produced by conventional techniques.

Those of the compounds of formula I in which E is a carboxy group and an adjacent pair of $R^1$, $R^2$, $R^3$ and $R^7$ are (a) an —OH group and hydrogen, or (b) an —OH group and a —COCH$_3$ group, are useful as intermediates in the production, by methods analogous to process (a) above, of a compound of formula XII,

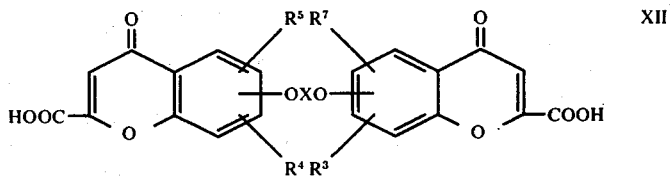

in which $R^4$, $R^5$ and X are as defined above and $R^3$ and $R^7$ are the remaining groups of $R^1$, $R^2$, $R^3$ and $R^7$ as defined above. The compounds of formula XII are themselves, or in the form of their sodium salts, useful at a dosage of 1 to 50 mgs. in the relief or prevention of allergic airway obstruction, e.g. the treatment of allergic asthma.

The compounds of formula I and their pharmaceutically acceptable derivatives, for example their pharmaceutically acceptable salts, esters and amides, e.g. their sodium, lower alkylamine, e.g. ethylamine, and hydroxy - substituted lower alkylamine, salts, are also useful because they possess pharmacological properties. In particular the compounds are antagonists of the slow-reacting substance of anaphylaxis (SRS-A), or its pathological effects, as is indicated by their activity in the test set out in Example A. The compounds also antagonise the effects of SRS-A obtained during antigen challenge of sensitized human chopped lung on isolated guinea pig ileum as described in Example A. The compounds also have the same utility at the same dosages as the compounds of Dutch Patent Specification No. 6811740.

The compounds are thus useful in the treatment of disorders in which SRS-A is a factor, for example skin afflictions, hay fever and obstructive airways diseases, e.g. asthma.

For the above-mentioned uses, the dosage administered will, of course, vary depending upon the compound employed, mode of administration and treatment desired. However, in general satisfactory results are obtained when administered at a daily dosage of from about 1 milligram to about 10 milligrams per kilogram of animal body weight, preferably given in divided doses 2 to 4 times a day or in sustained release form. For the larger mammals, the total daily dosage is in the range of from about 50 milligrams to about 700 milligrams, and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds may be administered in admixture with a pharmaceutically acceptable adjuvant, diluent or carrier, the composition used depending on many factors including the disorder to be treated. The compounds may be administered parenterally by inhalation or topically.

The invention also provides a process for the production of a pharmaceutically acceptable salt of a compound of formula I, which process comprises treating a compound of formula I, an ester or amide thereof or another salt thereof with an appropriate base, e.g. a sodium base or with an appropriate salt by a metathetical process.

As a specific group we provide those compounds of formula I in which E is a carboxy group and an adjacent pair of $R^1$, $R^2$, $R^3$ and $R^7$ are not (a) an —OH group and hydrogen, or (b) an —OH group and a —COCH$_3$ group. Those compounds in which the —OXO— group is attached to the chromone group in the 7 position are preferred as are those compounds in which E is a tetrazole group.

It is preferred that $R^5$ is hydrogen and $R^4$ is hydrogen, lower alkyl or lower alkenyl. It is also preferred that $R^4$ should be in the 6 or 8 position.

It is preferred that no more than 3 of $R^1$, $R^2$, $R^3$ and $R^7$ are other than hydrogen. Preferred values of $R^1$, $R^2$, $R^3$, $R^4$, $R^5$ and $R^7$ are hydrogen, hydroxy, lower alkoxy, lower alkoxy substituted by phenyl, lower acyl (e.g. lower alkanoyl, lower alkenoyl, or lower alkenoyl substituted by an amino or a mono- or di-loweralkyl amino group), amino, lower acyl amino (e.g. lower alkanoylamino), lower alkenyl, halogen (e.g. chlorine, bromine or iodine) or lower alkyl.

Specific examples of values of $R^1$, $R^2$, $R^3$, $R^4$, $R^5$ and $R^7$ are hydrogen, hydroxy, methoxy, benzyloxy, acetyl, dimethylaminoacryloyl, amino, acetylamino, allyl, methyl, ethyl, propyl and butyl.

Preferred compounds of formula I are those in which $R^5$ is hydrogen, $R^4$ is hydrogen, propyl or allyl, $R^7$ is hydrogen, $R^1$ is hydrogen, propyl or allyl, $R^2$ is hydroxy and $R^3$ is acetyl.

The group X is preferably a straight chain alkylene group containing, for example, from 3 to 7 carbon atoms and optionally substituted by a hydroxy group.

In this specification and in the claims 'lower' is used to mean a group containing up to and including 6 carbon atoms.

The invention is illustrated, but in no way limited by the following Examples, in which temperatures are in ° C.

EXAMPLE 1

7-[5-(4-Acetyl-3-hydroxyphenoxy)pentyloxy]-4-oxo-4H-1-benzopyrancarboxylic acid a. 4-(5-Bromopentyloxy)-2-hydroxyacetophenone To a mixture of 34 parts of 1,5-dibromopentane, 9.2 parts of potassium carbonate and 0.5 parts of potassium iodide, in 100 parts of dry acetone, was added, dropwise with stirring, a solution of 20 parts of resacetophenone in 200 parts of dry acetone and the mixture heated under reflux for 18 hours.

The mixture was filtered while hot and the inorganic salts washed with hot acetone. The acetone solution was evaporated to leave an oil which was triturated with 200 parts of diethyl ether. The insoluble solid was filtered and the ethereal solution extracted with 2½% sodium hydroxide solution, washed with water, dried over magnesium sulphate, filtered and the solvent removed to leave an oil which solidified on standing. The solid was recrystallized from IMS to yield 13.6 parts of 4-(5-bromopentyloxy)-2-hydroxyacetophenone as colourless needles, melting point 63.5°–65° C.

Analysis: Found: C, 52.2; H, 5.81% $C_{13}H_{17}BrO_3$ requires: C, 51.83; H, 5.65% b. Ethyl 7-[5-(4-acetyl-3-hydroxyphenoxy)pentyloxy]-4-oxo-4H-1-benzopyran-2-carboxylate A mixture of 3.05 parts of 4-(5-bromopentyloxy)-2-hydroxy acetophenone, 2.34 parts of ethyl 7-hydroxy-4-oxo-4H-1-benzopyran-2-carboxylate, 1.38 parts of potassium carbonate and 0.5 parts of potassium iodide, in 200 parts of dry acetone, was heated under reflux for 24 hours. The solution was filtered while hot and the inorganic salts washed with hot acetone. The solvent was removed to leave a yellow solid, which was washed with water and ether. The insoluble yellow solid was crystallised from ethyl alcohol to yield 3.3 parts of ethyl 7-[5-(4-acetyl-3-hydroxyphenoxy)pentyloxy]-4-oxo-4H-1-benzopyran-2-carboxylate as pale yellow needles, melting point 136°–137° C.

Analysis: Found: C, 66.05; H, 5.74; $C_{25}H_{26}O_8$ requires: C, 66.05; H, 5.77.

c. 7-[5-(4-Acetyl-3-hydroxyphenoxy)pentyloxy]-4-oxo-4H-1-carboxylic acid

To a solution of 2.0 parts of ethyl 7-[5-(4-acetyl-3-hydroxyphenoxy)-pentyloxy]-4-oxo-4H-1-benzopyran-2-carboxylate in 100 parts of ethyl alcohol was added 2.0 parts of sodium bicarbonate and the mixture boiled on the steam can for 2 hours. During this period water was added and the ethyl alcohol allowed to evaporate.

The aqueous solution was filtered and acidified with dilute hydrochloric acid to give a white solid, which was filtered and crystallised from ethyl alcohol and dioxan to yield 1.6 parts of 7-[5-(4-acetyl-3-hydroxyphenoxy)pentyloxy]-4-oxo-4H-1-benzopyran-2-carboxylic acid as off white needles, melting point 226°–228° C.

Analysis: Found: C, 64.4; H, 5.34; $C_{23}H_{22}O_8$ requires: C, 64.78; H, 5.20.

d. 7-[5-(4-Acetyl-3-hydroxyphenoxy)pentyloxy]-4-oxo-4H-1-benzopyran-2-carboxylic acid sodium salt A mixture of 3.35 parts of 7-[5-(4-acetyl-3-hydroxyphenoxy) pentyloxy]-4-oxo-4H-1-benzopyran-2-carboxylic acid and 0.66 parts of sodium bicarbonate in 200 parts of water, was heated to effect solution. The solution was filtered while hot and on cooling a white solid crystallised. This was filtered, washed with ice-cold water and dried under vacuum over phosphorus pentoxide to yield 3.0 parts of 7-[5-(4-acetyl-3-hydroxyphenoxy) pentyloxy]-4-oxo-4H-1-benzopyran-2-carboxylic acid sodium salt, melting point 210° C (indefinite).

Analysis: Found: C, 60.7; H, 4.57; $C_{23}H_{21}NaO_8$ ½$H_2O$ requires: C, 60.4; H, 4.81.

EXAMPLE 2

Using the same process as in Example 1, but substituting appropriate starting materials, the compounds (and their sodium salts) shown in Table I were made.

TABLE I

| Compound | Analysis | m.p. °C | Analysis of sodium salt |
|---|---|---|---|
| 8-Allyl-7-[5-(4-acetyl-2-allyl-3-hydroxy-phenoxy)pentyloxy]-4-oxo-4H-1-benzopyran-2-carboxylic acid | Found: C, 68.9; H, 6.08 Requires: C, 68.76; H, 5.97 | 196–7 | |
| 8-Allyl-7-[5-(4-acetylphenoxy)pentyloxy]-4-oxo-4H-1-benzopyran-2-carboxylic acid | Found: C, 69.60; H, 5.94 Requires: C, 69.32; H, .82 | 201–3 | $C_{26}H_{25}NaO_7 \cdot \tfrac{1}{2}H_2O$ Found: C, 65.45; H, 5.22 Requires: C, 65.15; H, 5.43 |
| 8-Allyl-7-[5-(2-acetyl-3-hydroxyphenoxy)pentyloxy]-4-oxo-4H-1-benzopyran-2-carboxylic acid | Found: C, 67.4; H, 5.67 Requires: C, 67.0; H, 5.62 | 171–4 | |
| 8-Allyl-7-[5-(4-acetyl amino phenoxy)pentyloxy]-4-oxo-4H-1-benzopyran-2-carboxylic acid | Found: C, 65.65; H, 5.75 N, 2.84 Requires: C, 65.7; H, 5.80 N, 2.95 $C_{26}H_{27}NO_7 \cdot \tfrac{1}{2}H_2O$ | 126–8 | $C_{26}H_{26}NNaO_7 \cdot H_2O$ Found: C, 61.8; H, 5.28 N, 2.62 Requires: C, 61.8; H, 5.54 N, 2.77 |
| 7-[5-(4-Acetylphenoxy)pentyloxy]-4-oxo-4H-1-benzopyran-2-carboxylic acid | Found: C, 67.15; H, 5.42 Requires: C, 67.30; H, 5.40 | 219–221 | |
| 7-[5-(3-Methoxyphenoxy)pentyloxy]-4-oxo-4H-1-benzopyran-2-carboxylic acid | Found: C, 66.45; H, 5.67 Requires: C, 66.32; H, 5.57 | 155–7 | $C_{22}H_{21}NaO_7 \cdot \tfrac{1}{2}H_2O$ Found: C, 61.7; H, 4.94 Requires: C, 61.5; H, 5.13 |
| 7-[5-(3-Benzyloxy phenoxy)pentyloxy]-4-oxo-4H-1-benzopyran-2-carboxylic acid | Found: C, 70.9; H, 5.52 Requires: C, 71.2; H, 5.51 | 152–3 | $C_{28}H_{25}NaO_7 \cdot H_2O$ Found: C, 65.8; H, 5.29 Requires: C, 65.4; H, 5.25 |
| 7-[5-(2-Acetyl-4-allyl-3-hydroxyphenoxy)pentyloxy]-4-oxo-4H-1-benzopyran-2-carboxylic acid | Found: C, 66.94; H, 5.62 Requires: C, 66.55; H, 5.59 | 159–160 | $C_{26}H_{25}NaO_8 \cdot 1\tfrac{1}{2}H_2O$ Found: C, 61.71; H, 5.0 Requires: C, 61.31; H, 5.5 |
| 4-Oxo-7-[5-(2-propylphenoxy)pentyloxy]-4H-1-benzopyran-2-carboxylic acid | Found: C, 70.3; H, 6.5 Requires: C, 70.2; H, 6.3 | 151 | $C_{24}H_{25}NaO_6 \cdot \tfrac{1}{2}H_2O$ Found: C, 64.8; H, 6.0 Requires: C, 65.4; H, 5.9 |
| 7-[5-(2-t-Butylphenoxy)pentyloxy]-4-oxo-4H-1-benzopyran-2-carboxylic acid | Found: C, 70.7; H, 6.7 Requires: C, 70.7; H, 6.65 | 171–172 | $C_{25}H_{27}NaO_6 \cdot H_2O$ Found: C, 65.1; H, 6.3 Requires: C, 64.7; H, 6.3 |

EXAMPLE 3

8-Allyl-7-[3-(4-acetyl-2-allyl-3-hydroxyphenoxy)-2-hydroxypropoxy]-4-oxo-4H-1-benzopyran-2-carboxylic acid a. 3-Allyl-4-(2,3-epoxypropoxy)-2-hydroxyacetophenone To a solution of 19.2 parts of 3-allyl-2,4-dihydroxyaceto phenone and 24.0 parts of 1-chloro-2,3-epoxypropane in 15 parts of ethyl alcohol, heated under reflux, was added a solution of 6.6 parts of potassium hydroxide in 3.0 parts of water and 25.0 parts of ethyl alcohol, dropwise with stirring, and the mixture stirred and heated under reflux for 2 hours.

Water and ether were added, the ether layer was separated, dried over magnesium sulphate, filtered and the solvent removed to leave a yellow oil. The oil was distilled at reduced pressure to yield 16.1 parts of 3-allyl-4(2,3-epoxypropoxy)-2-hydroxyacetophenone as a white solid, melting point 66°–67.5° C.

Analysis: Found: C, 67.6; H, 6.21; $C_{14}H_{16}O_4$ requires: C, 67.73; H, 6.50.

b. Ethyl 8-allyl-7-hydroxy-4-oxo-4H-1-benzopyran-2-carboxylate

To a stirred solution of sodium ethoxide in ethyl alcohol, prepared from 2.3 parts of sodium and 50.0 parts of ethyl alcohol, was added a slurry of 4.8 parts of 3-allyl-2,4-dihydroxyacetophenone and 9.15 parts of diethyl oxalate in 50.0 parts of diethyl ether. The mixture was stirred and heated under reflux for 4 hours.

Water and diethyl ether were added and the aqueous layer was separated, acidified with dilute hydrochloric acid, and extracted with ethyl acetate. The organic layer was separated, dried over magnesium sulphate and the solvent removed to leave a red oil. The oil was dissolved in ethyl alcohol and 0.5 parts of concentrated hydrochloric acid were added and the mixture heated under reflux for 15 minutes. The solvent was removed to leave an oil which was dissolved in ethyl acetate and washed with sodium bicarbonate solution. The organic layer was separated and evaporated to a yellow solid which was crystallised from diethyl ether to yield 3.6 parts of ethyl 8-allyl-7-hydroxy-4-oxo-4H-1-benzopyran-2-carboxylate as a pale yellow solid, melting point 164°–165° C.

Analysis: Found: C, 65.1; H, 4.98; $C_{15}H_{14}O_5$ requires: C, 65.6; H, 5.15.

c. 8-Allyl-7-[3-(4-acetyl-2-allyl-3-hydroxyphenoxy)-2-hydroxypropoxy]-4-oxo-4H-1-benzopyran-2-carboxylic acid To a solution of 5.5 parts of ethyl 8-allyl-7-hydroxy-4-oxo-4H-1-benzopyran-2-carboxylate and 5.0 parts of 4-(2,3-epoxypropoxy)-3-allyl-2-hydroxyacetophenone in 50 parts of dimethylformamide was added 0.5 parts of benzyltrimethyl ammonium hydroxide and the mixture heated under reflux for 4 hours.

The solvent was removed to leave a brown oil, which was dissolved in ethyl acetate and extracted with 0.5N sodium hydroxide, dried over magnesium sulphate, filtered, and evaporated to dryness.

The oil remaining was dissolved in ethanol and hydrolysed by boiling with an aqueous solution of sodium bicarbonate. The solution was extracted with ether and the aqueous layer separated and acidified with dilute hydrochloric acid. The precipitated solid was filtered and added to 50 parts of saturated sodium bicarbonate solution to give a precipitate of the insoluble sodium salt. The solid was filtered, washed with 10 parts of cold water and the resultant white solid dissolved in hot water and acidified with dilute hydrochloric acid to yield 3.0 parts of 8-allyl-7-[3-(4-acetyl-2-allyl-3-hydroxyphenoxy)-2-hydroxypropoxy]-4-oxo-4H-1-benzopyran-2-carboxylic acid, crystallised from benzene as a pale yellow solid, melting point 105° C (indefinite).

Analysis: Found: C, 63.7; H, 5.20; $C_{27}H_{26}O_9 \cdot \tfrac{1}{2}H_2O$ requires: C, 64.3; H, 5.37.

d. 8-Allyl-7-[3-(4-acetyl-2-allyl-3-hydroxyphenoxy)-2-hydroxypropoxy]-4-oxo-4H-1-benzopyran-2-carboxylic acid sodium salt A solution of 3.5 parts of 8-allyl-7-[3-(4-acetyl-2-allyl-3-hydroxyphenoxy)-2-hydroxypropoxy]-4-oxo- 4H-1-benzopyran-2-carboxylic acid and 0.584 parts of sodium bicarbonate in 500 parts of water was freeze dried to yield 3.5 parts of 8-allyl-7-[3-(4-acetyl-2-allyl-3-hydroxyphenoxy)-2-hydroxypropoxy]-4-oxo-4H-1-benzopyran-2-carboxylic acid sodium salt as a white solid, melting point 249°–251° C.
Analysis: Found: C,62.7; H, 4.90; $C_{27}H_{25}NaO_9$ requires: C, 62.8; H, 4.88.

EXAMPLE 4

Using the same process as in Example 3, but substituting appropriate starting materials, the compounds (and their sodium salts) shown in Table II were made.

TABLE II

| Compound | Analysis | m.p.° C | Analysis of sodium salt |
|---|---|---|---|
| 7-[3-(4-Acetyl3-hydroxyphenoxy)-2-hydroxypropoxy]-4-oxo-4H-1-benzopyran 2-carboxylic acid | Found: C, 60.0 H, 4.28<br>Requires: C, 59.6 H, 4.49 $C_{21}H_{18}O_9 \cdot \frac{1}{2}H_2O$ | 251–2 | |
| 8-Allyl-7-[3-(4-acetyl-3-hydroxy-phenoxy)-2-hydroxypropoxy]-4-oxo-4H-1-benzopyran-2-carboxylic acid | Found: C, 61.8 H, 5.12<br>Requires: C, 62.2 H, 4.97 $C_{24}H_{22}O_9 \cdot \frac{1}{2}H_2O$ | 205 | Found: C, 58.5 H, 4.33<br>Requires: C, 58.3 H, 4.61 $C_{24}H_{21}NaO_9 \cdot H_2O$ |
| 7-[3-(4-Acetyl-3-hydroxy-2-allyl-phenoxy)-2-hydroxypropoxy]-4-oxo 4H-1-benzopyran-2-carboxylic acid | Found: C, 59.8 H, 4.95<br>Requires: C, 59.9 H, 5.19 $C_{24}H_{22}O_9 \cdot 1\frac{1}{2}H_2O$ | 120–5 | |
| 8-Propyl-7-[3-(4-acetyl-3-hydroxy-2-propylphenoxy)-2-hydroxypropoxy]-4-oxo-4H-1-benzopyran-2-carboxylic acid | Found: C, 64.7 H, 6.22<br>Requires: C, 65.0 H, 6.11 $C_{27}H_{30}O_9$ | 206–7 | Found: C, 59.44 H, 5.74<br>Requires: C, 59.23 H, 5.85 $C_{27}H_{29}NaO_9 \cdot 1\frac{1}{2}H_2O$ |
| 4-Oxo-8-propyl-7-[3-(2-propylphenoxy)-2-hydroxypropoxy]-4H-1-benzopyran-2-carboxylic acid | Found: C, 67.87 H, 6.48<br>Requires: C, 68.17 H, 6.41 $C_{25}H_{28}O_7$ | 129–130 | |
| 4-Oxo-7-[3-(2-propylphenoxy)-2-hydroxypropoxy]-4H-1-benzopyran-2-carboxylic acid | Found: C, 66.62 H, 5.66<br>Requires: C, 66.32 H, 5.57 $C_{22}H_{22}O_7$ | 174–175 | |
| 7-[3-(2-Allylphenoxy)-2-hydroxypropoxy]-4-oxo-4H-1-benzopyran-2-carboxylic acid | Found: C, 66.38 H, 5.24<br>Requires: C, 66.66 H, 5.09 $C_{22}H_{20}O_7$ | 181–183 | |
| 7-[3-(4-Acetyl-3-hydroxy-2-propylphenoxy)-2-hydroxypropoxy]-4-oxo-4H-1-benzopyran-2-carboxylic acid hemihydrate | Found: C, 61.89 H, 5.10<br>Requires: C, 61.90 H, 5.37 $C_{24}H_{26}O_9 \cdot \frac{1}{2}H_2O$ | 194–195 | |
| 7-[3-(4-Acetyl-3-hydroxy-2-propylphenoxy)-2-hydroxypropoxy]-4-oxo-6-propyl-4H-1-benzopyran-2-carboxylic acid | Found: C, 64.93; H, 6.08<br>Requires: C, 65.06; H, 6.02 $C_{27}H_{30}O_9$ | 205 | |
| 4-oxo-6-Propyl-7-[3-(2-propylphenoxy)-2-hydroxypropoxy]-4H-1-benzopyran-2-carboxylic acid | Found: C, 68.0 H, 6.4<br>Requires: C, 68.2 H, 6.4 $C_{25}H_{28}O_7$ | 215–216 | Found: C, 61.9 H, 6.0<br>Requires: C, 61.4 H, 6.1 $C_{25}H_{27}NaO_7 \cdot 1\frac{1}{2}H_2O$ |
| 7-[2-Hydroxy-3-(2,4-dimethylphenoxy)propoxy]-4-oxo-4H-1-benzopyran-2-carboxylic acid | Found: C, 65.4 H, 5.3<br>Requires: C, 65.6 H, 5.2 $C_{21}H_{20}O_7$ | 179–181 | Found: C, 56.2 H, 5.4<br>Requires: C, 56.1 H, 5.3 $C_{21}H_{19}NaO_7 \cdot 2\frac{1}{2}H_2O$ |
| 7-[3-(2,4-Di-t-butylphenoxy)-2-hydroxypropoxy]-4-oxo-4H-1-benzopyran-2-carboxylic acid | Found: C, 69.6 H, 7.0<br>Requires: C, 69.2 H, 6.9 $C_{27}H_{32}O_7$ | 227–228 | Found: C, 62.6 H, 6.6<br>Requires: C, 62.7 H, 6.2 $C_{27}H_{29}NaO_9 \cdot 1\frac{1}{2}H_2O$ |
| 7-(3-[2-t-Butylphenoxy]-2-hydroxypropoxy)-4-oxo-4H-1-benzopyran-2-carboxylic acid | Found: C, 63.9 H, 6.1<br>Requires: C, 64.2 H, 6.0 $C_{23}H_{24}O_7 \cdot H_2O$ | 157–158 | Found: C, 60.4 H, 5.7<br>Requires: C, 59.9 H, 5.65 $C_{23}H_{23}NaO_7 \cdot 3/2H_2O$ |

EXAMPLE 5

7-[5-(4-Oxo-4H-1-benzopyran-7-yloxy)pentyloxy]4-oxo-4H-1-benzopyran-2- carboxylic acid a. 7-(5-Bromopentyloxy)-4-oxo-4H-1-benzopyran-2-carboxylic acid; ethyl ester 20 parts of 7-hydroxy-4-oxo-4H-1-benzopyran-2-carboxylic acid ethyl ester were stirred and refluxed with 40 parts dibromopentane and 12 parts potassium carbonate in 600 parts by volume of dry acetone. The mixture was refluxed for 18 hr., cooled and filtered. The acetone filtrate was evaporated to dryness to give an oil. Petroleum ether (40°–60°) was added and after some time the oil slowly solidified to give a sticky solid. This crude product was purified by dissolving it in benzene and slowly adding petroleum ether (40°–60°). 10.2 parts of 7-(5-bromopentyloxy)-4-oxo-4H-1-benzopyran-2-carboxylic acid; ethyl ester separated out as a white solid, m.p. 72°–8°, raised to 78°–79°, (from petroleum ether 60°–80°).

Analysis: Found: C, 53.5; H, 4.99%; $C_{17}H_{19}O_5Br$ requires: C, 53.3; H, 4.96%.

b. 7-[5-(4-oxo-4H-1-benzopyran-7-yloxy)pentyloxy]4-oxo-4H-1-benzopyran 2-carboxylic acid, ethyl ester A mixture of 4.6 parts of 7-(5-bromopentyloxy)4-oxo-4H-1-benzopyran-2-carboxylic acid, ethyl ester, 2 parts of ethyl 7-hydroxychromone-2-carboxylate,1,8 parts of potassium carbonate, a few potassium iodide crystals and 80 parts by volume of dry acetone was refluxed on a steam bath for 20 hr. The cooled mixture was filtered and the filtrate evaporated down to give an oil which when treated with petroleum ether (40°–60°), solidified to give 4.0 parts of crude product. Crystallisation from ethanol gave 2.9 parts of 7-[5-(4-oxo-4H-1-benzopyran-7-yloxy)pentyloxy]-4-oxo-4H-1-benzopyran-2-carboxylic acid; ethyl ester, m.p. 113°–116°.

Analysis: Found: C, 67.1; H, 5.16%; $C_{26}H_{24}O_8$ requires: C, 67.23; H, 5.21%.

c. 7-[5-(4-Oxo-4H-1-benzopyran-7yloxy)pentyloxy]4-oxo-4H-1benzopyran-2-carboxylic acid A mixture of 5 parts of the ethyl ester from (b), 5 parts of sodium bicarbonate, 70 parts by volume of water and 20 parts by volume of ethanol was warmed and stirred on a steam bath for 30 min. The cooled aqueous solution on acidification gave 4.6 parts of the required acid, m.p. 228°–222° C.

Analysis: Found: C, 65.8; H, 4.7%; $C_{24}H_{20}O_8$ requires: C, 66.05; H, 4.62%.

d. 7-[5-(4-Oxo-4H-1-benzopyran-7-yloxy)pentyloxy]4-oxo-4H-1-benzopyran-2-carboxylic acid; sodium salt 0.69 of a part of sodium bicarbonate was added in small portions to 3.9 parts of the acid in 100 parts by volume of water. The solution was gently heated until nearly all the acid was in solution. The neutral solution was filtered and freeze dried to give 3.6 parts of the sodium salt.

EXAMPLE 6

7-[3-(4-Oxo-4H-1-benzopyran-7-yloxy)-2-hydroxypropoxy]7-oxo-4H-1-benzopyran-2-carboxylic acid a. 7-(2,3-Epoxypropoxy)-4-oxo-4H-1-benzopyran-2-carboxylic acid; ethyl ester A mixture of 10 parts 7-hydroxy-4-oxo-4H-1-benzopyran-2carboxylic acid; ethyl ester, 15 parts epibromohydrin, 6 parts potassium carbonate and 150 parts by volume of dry acetone was stirred and refluxed for 18 hr. The cooled mixture was filtered and the filtrate evaporated down to give an oil, which solidified. This crude product was dissolved in ethyl acetate which was washed with sodium carbonate solution. The dried ethyl acetate extract on evaporation gave 7 parts of the ethyl ester, m.p. 124°–127°. crystallisation from ethanol gave 6.3 parts of pure ethyl ester, m.p. 126°–128°.

Analysis: Found: C, 62.2; H, 4.87%; $C_{15}H_{14}O_6$ requires: C, 62.06; H, 4.86%.

b. 7-[3-(4-Oxo-4H-1-benzopyran-7-yloxy)-2-hydroxypropoxy]-4-oxo-4H-1-benzopyran-2-carboxylic acid A mixture of 7.16 parts 7-(2,3-epoxypropoxy)-4-oxo-4H-1-benzopyran-2- carboxylic acid; ethyl ester, 4 parts ethyl 7-hydroxy chromone-2-carboxylate, 12 drops of Triton B, and 80 parts by volume of dimethyl formamide, was stirred and refluxed for 6 hr. The dimethylformamide, was evaporated off and the residual oil extracted well with ethyl acetate leaving a sticky solid. The ethyl acetate extracts were washed with sodium carbonate, dried and evaporated to give the crude ethyl ester of the required acid. Crystallisation of this solid from ethanol gave 0.69 of a part of this ester m.p. 152°–6°.

A mixture of 0.5 of a part of this ester, 0.1 of a part of sodium bicarbonate, 8 parts by volume of water and 2 parts by volume of ethanol was warmed on a steam bath for 2½ hr. The filtered solution on acidification gave 0.4 of a part of the required crude acid, m.p. 220°–225°. Crystallisation from ethanol gave 0.36 of a part of the required acid, m.p. 243°–247°.

Analysis: Found: C, 61.7; H, 3.8%; $C_{22}H_{16}O_9$ requires: C, 62.28; H, 3.8%.

c. 7-[3-(4-Oxo-4H-1-benzopyran-7-yloxy)-2-hydroxypropoxy]-4-oxo-4H-1-benzopyran-2-carboxylic acid; sodium salt 0.039 of a part of sodium bicarbonate was added to 0.198 of a part of the above acid in 12 parts by volume of water. The solution was gently heated until it became neutral. The cooled solution was filtered and freeze-dried to give 0.2 of a part of the sodium salt.

EXAMPLE 7

7-[3-(4-Acetyl-3-hydroxy-2-propylphenoxy)-2-hydroxypropoxy]-4-oxo-8-propyl-4H-1-benzopyran-2-carboxylic acid tris (hydroxymethyl) methylamine salt monohydrate A solution of 0.121 parts of tris (hydroxymethyl) methylamine in 25 parts of ethyl alcohol was added to a solution of 0.498 parts of 7-[3-(4-acetyl-3-hydroxy-2-propylphenoxy)-2-hydroxyporpoxy]-4-oxo-8-propyl-4H-1-benzopyran-2-carboxylic acid in 25 parts of ethyl alcohol and the mixture heated on the steam bath for 5 minutes.

The solvent was removed under reduced pressure and 50 parts water added. The solution was filtered and freeze dried to yield 0.6 parts of 7-[3-(4-acetyl-3-hydroxy-2-propylphenoxy)-2-hydroxypropoxy]-4-oxo-8-propyl-4H-1-benzopyran-2-carboxylic acid tris (hydroxymethyl)methylamine salt, monohydrate.

Analysis: Found: C, 58.49; H, 6.64; N, 2,18; $C_{31}H_{41}NO_2.H_2O$ requires: C, 58.31; H, 6.74; N, 2.19.

EXAMPLE 8

7-[3-(4-acetyl-3-hydroxy-2-propylphenoxy)propoxy]-4-oxo-8-propyl-4H-1-benzopyran-2-carboxylic acid a. 4-(3-Bromopropoxy)-2-hydroxy-3-propylacetophenone A solution of 7.2 parts of sodium hydroxide in 100 parts of water was added slowly over one hour to a stirred, refluxing mixture of 144 parts of 1,3-dibromopropane, 35 parts of 2,4-dihydroxy-3-propylacetophenone, and 300 parts of water. The mixture was heated for 5 hours and then stirred at room temperature overnight. The organic phase was separated, and the aqeuous phase was extracted with chloroform. The organic layers were combined and evaporated to an oil which was distilled to give a fraction boiling at 32–36/0.02 mm., which was mostly 1,3-dibromopropane, and a fraction boiling at 172°–180°/0.02 mm. which consisted of 23.5 parts of 4-(3-bromopropoxy)-2-hydroxy-3-propylacetophenone.

b. 7-[3-(4-Acetyl-3-hydroxy-2-propylphenoxy)-propoxy]-4-oxo-8-propyl-4H-1-benzopyran-2-carboxylic acid A mixture of 16 parts of ethyl 7-hydroxy-4-oxo-8-propyl-4H-1-benzopyran-2-carboxylate, 23.5 parts of 4-(3-bromopropoxy)-2-hydroxy-3-propylacetophenone, 10.7 parts of anhydrous potassium carbonate, 0.5 parts of potassium iodide, and 300 parts of dry acetone was refluxed for 18 hours, and the hot solution was filtered. The residue was washed with hot acetone, and the combined filtrates were evaporated to an oil. The oil was dissolved in chloroform and washed with 1% sodium hydroxide solution, and water, dried and evaporated to an oil, which was hydrolysed by boiling with an aqueous ethanolic solution of 5.5 parts of sodium bicarbonate over one hour. The reaction mixture was diluted with about 8000 parts of warm and washed with ethyl acetate. Acidification of the aqueous layer gave a solid, which was taken up in 500 parts of hot ethanol, and to this was added a dilute aqueous solution of sodium bicarbonate. The mixture was allowed to cool with the addition of small portions of ethanol to prevent gel formation. A gelatinous precipitate of the sodium salt was obtained which was filtered off and washed with water. The precipitate was suspended in water and acidified to give a solid, which was recrystallised from ethyl acetate to afford 6.6 parts 7-[3-(4-acetyl-3-hydroxy-2-propylphenoxy)propoxy]-4-oxo-8-propyl-4H-1-benzopyran-2-carboxylic acid, m.p. 173°–174°.

Analysis: Found: C, 67.13; H, 6.30%; $C_{27}H_{30}O_8$ requires: C, 67.20; H, 6.27%.

c. Sodium 7-[3-(4-acetyl-3-hydroxy-2-propylphenoxy)propoxy]-4-oxo-8-propyl-4H-1-benzopyran-2-carboxylate To 5.0 parts of 7-[3-(4-acetyl-3-hydroxy-2-propyl phenoxy) propoxy]-4-oxo-8-propyl-4H-1-benzopyran-2-carboxylic acid dissolved in 200 parts of hot ethanol was added a solution of 0.870 parts of sodium bicarbonate in 30 parts of water. The solution was evaporated under reduced pressure to dryness, dry benzene was added and the mixture was again evaporated to dryness. The resulting buff solid was ground to a powder and dried to afford 5.0 parts of sodium 7-[3-(4-acetyl-3-hydroxy-2-propylphenoxy)propoxy]-4-oxo-8-propyl-4H-1-benzopyran-2-carboxylate.

EXAMPLE 9

The compounds shown below were made using the techniques described in Example 8 and appropriate starting materials.

TABLE III

| Compound | Analysis | m.p. °C | Analysis of sodium salt |
|---|---|---|---|
| 4-Oxo-8-propyl-7-[3-(2-propylphenoxy)propoxy]-4H-1-benzopyran-2-carboxylic acid | Found: C, 70.4 H, 6.6 Requires: C, 70.7 H, 6.65 $C_{25}H_{28}O_6$ | 162–163 | Found: C, 67.5 H, 6.3 Requires: C, 67.2 H, 6.05 $C_{25}H_{27}NaO_6$ |
| 4-Oxo-6-propyl-7-[3-(2-propylphenoxy)propoxy]-4H-1-benzopyran-2-carboxylic acid | Found: C, 70.3 H, 6.6 Requires: C, 70.7 H, 6.65 $C_{25}H_{28}O_6$ | 138–139 | Found: C, 66.5 H, 6.1 Requires: C, 66.1 H, 6.2 $C_{25}H_{27}NaO_6 \cdot \tfrac{1}{2}H_2O$ |

EXAMPLE 10

8-(3-[2-t-Butylphenoxy]-2-hydroxypropoxy)-4-oxo-4H-1-benzopyran-2-carboxylic acid a. 3-(2-t-Butylphenoxy)-1,2-epoxypropane To a solution of 40 parts of o-t-butylphenol, 75 parts of epichlorhydrin, and 40 parts of ethanol boiling under reflux with stirring was added dropwise over 10 minutes a solution of 17.6 parts of potassium hydroxide dissolved in 66 parts of ethanol and the minimum amount of water. The mixture was stirred and refluxed for 105 minutes, cooled, diluted with water, and well extracted with ether, which was then washed with water, dried over magnesium sulphate, and evaporated to an oil. Distillation at 144°/8 mm afforded 43 parts of 3-(2-t-butylphenoxy)-1,2-epoxypropane as a clear oil.

Analysis: Found: C, 75.5; H, 8.9; $C_{13}H_{18}O_2$ requires: C, 75.7; H, 8.8%.

b. 8-(3-[2-t-Butylphenoxy]-2-hydroxypropoxy)-4-oxo-4H-1-benzopyran-2-carboxylic acid A mixture of 16.7 parts of ethyl 8-hydroxy-4-oxo-4H-1-benzopyran-2-carboxylate, 14.7 parts of 3-(2-t-butylphenoxy)-1,2-epoxypropane, 50 parts of dimethyl formamide, and 0.1 parts of benzyltrimethyl ammonium hydroxide was boiled under reflux for 3 hours, evaporated to leave a dark brown oil, and treated with ethyl acetate, which was then washed with 2% sodium hydroxide solution, and water, dried, and evaporated to an oil. The oil was chromatographed on a silica column with chloroform as eluent to give a gummy solid, which was boiled with an aqueous ethanolic solution of sodium bicarbonate. The mixture was acidified to give a solid, which was recrystallised from ethanol after treatment with charcoal to give 4.6 parts of 8-(3-[2-t-butylphenoxy]-2-hydroxypropoxy)-4-oxo-4H-1-benzopyran-2-carboxylic acid as a cream solid, mp. 227°–228° (decomp.).

Analysis: Found: C, 65.3; H. 6.0; $C_{23}H_{24}O_7 \cdot \frac{1}{2}H_2O$ requires: C, 65.6; H, 6.1%.

c. Sodium 8-(3-[2-t-butylphenoxy]-2-hydroxypropoxy)-4-oxo-4H-1-benzopyran-2carboxylate sesquihydrate To a hot solution of 4.238 parts of 8-(3-2-t-butylphenoxy-2-hydroxypropoxy)-4-oxo-4H-1-benzopyran-2carboxylic acid in 250 parts of ethanol was added a solution of 0.882 parts of sodium bicarbonate in 50 parts of water. The resulting solution was filtered and allowed to cool to give 4.0 parts of sodium 8-(3-[2-t-butylphenoxy]-2-hydroxypropoxy)-4-oxo-4H-1-benzopyran-2-carboxylate sesquihydrate after collecting and drying over phosphorus pentoxide.

Analysis: Found: C, 59.8; H, 5.8; $C_{23}H_{23}NaO_7 \cdot 3/2\text{-}H_2O$ requires: C, 59.9; H, 5.6%.

EXAMPLE 11

The compounds shown below were made using the techniques described in Example 10 and the appropriate starting materials.

TABLE IV

| Compound | Analysis | m.p. °C | Analysis of sodium salt |
|---|---|---|---|
| 8-[2-Hydroxy-3-(2-iodophenoxy)-propoxy]-4-oxo-4H-1-benzopyran-2-carboxylic acid | Found: C, 47.4 H, 3.3 I, 26.3<br>Requires: C, 47.4 H, 3.1 I, 26.3 $C_{19}H_{15}IO_7$ | 200–201 | Found: C, 44.4 H, 3.0<br>Requires: C, 44.4 H, 2.9 $C_{19}H_{14}INaO_7 \cdot \frac{1}{2}H_2O$ |
| 8-[3-(2-n-butylphenoxy)-2-hydroxypropoxy]-4-oxo-4H-1-benzopyran-2-carboxylic acid | Found: C, 66.9 H, 5.9<br>Requires: C, 66.9 H, 5.9 $C_{23}H_{24}O_7$ | 157–158 | Found: C, 59.2 H, 5.7<br>Requires: C, 58.8 H, 5.7 $C_{23}H_{23}NaO_7 \cdot 2H_2O$ |
| 8-[2-Hydroxy-3-(2-propylphenoxy)propoxy]-4-oxo-4H-1-benzopyran-2-carboxylic acid | Found: C, 66.2 H, 5.6<br>Requires: C, 66.3 H, 5.6 $C_{22}H_{22}O_7$ | 160 | Found: C, 59.9 H, 5.45<br>Requires: C, 60.3 H, 5.25 $C_{22}H_{21}NaO_7 \cdot H_2O$ |

EXAMPLE 12

8-(3-[2-n-butylphenoxy]propoxy)-4-oxo-4H-1-benzopyran-2-carboxylic acid a. 3-Bromopropyl-2-n-butylphenyl ether A solution of 30 parts of o-n-butylphenol in 150 parts of dry acetone was added dropwise over 5 hours to a stirred refluxing suspension of 80.8 parts of 1,3-dibromopropane, 27.6 parts of anydrous potassium carbonate and 0.5 parts of potassium iodide in 170 parts of dry acetone.

The mixture was refluxed for a further 16½ hours, and filtered. The residue was well washed with hot acetone and the combined filtrates were evaporated to an oil, which was dissolved in ether, washed with 10% sodium hydroxide solution and water, dried and evaporated. The residue was distilled at 160°–167°/10 mm to afford 33 parts of 3-bromopropyl 2-n-butylphenyl ether as a clear oil.

b. 8-[3-(2-n-butylphenoxy)propoxy]-4-oxo-4H-1-benzopyran-2-carboxylic acid

A porous thimble containing 11.7 parts of ethyl 8-hydroxy-4-oxo-4H-1-benzopyran-2-carboxylate in a soxhlet apparatus was extracted by the condensate into a stirred refluxing mixture of 14.9 parts 3-bromopropyl-2-n-butylphenyl ether, 13.8 parts of anhydrous potassium carbonate, 0.5 parts of potassium iodide and 300 parts of dry acetone. The mixture was refluxed for a further 27 hours, and filtered. The filtrate was evaporated to a dark red liquid.

A mixture of 20.6 parts of the red liquid, 20.0 parts of sodium bicarbonate and 150 parts of ethanol were boiled while water was slowly added to make up the volume as the ethanol was removed. When hydrolysis was complete the part aqueous solution was washed with ether, cooled and acidified to afford a cream solid. Crystallisation from aqueous ethanol afforded 8.2 parts of 8-[3-(2-n-butyl phenoxy)propoxy]-4-oxo-4H-1-benzopyran-2-carboxylic acid mp 168°–168.5° C.

Analysis: Found: C, 69.6; H, 6.2; $C_{23}H_{24}O_6$ requires: C, 69.7; H, 6.1%.

c. Sodium 8-[3-(2-n-butylphenoxy)propoxy]-4-oxo-4H-1-benzopyran 2-carboxylate monohydrate A mixture of 8.0 parts of 8-[3-(2-n-butylphenoxy)propoxy]-4-oxo-4H-1-benzopyran-2-carboxylate, 1.696 parts of sodium bicarbonate and 600 parts of water was heated to effect solution. The hot solution was filtered, allowed to cool to give a solid, which was collected and dried under vacuum over calcium chloride to furnish 8.2 parts of sodium 8-[3-(2-n-butyl-phenoxy) propoxy] - 4 - oxo - 4H -1- benzopyran -2-carboxylate monohydrate.

Analysis: Found: C, 63.5; H, 5.9; $C_{23}H_{23}NaO_6 \cdot 1H_2O$ requires C, 63.3; H, 5.8%.

EXAMPLE 13

4-Oxo-8-[7-(2-n-propylphenoxy)heptyloxy]-4H-1-benzopyran-2-carboxylatic acid a. 7-Bromoheptyl 2-n-propylphenyl ether A mixture of 17 parts of 2-propylphenyl, 97 parts of 1,7-dibromoheptane, 2 parts of potassium iodide and 60 parts of anhydrous potassium carbonate was refluxed in 1000 parts of anhydrous acetone for 65 hours. After filtration the organic layer was concentrated and washed with 200 parts of 1% sodium hydroxide solution. The alkaline layer was washed four times with 100 parts of ether, the combined ethereal extracts and organic layer washed with water, dried over magnesium sulphate and evaporated to yield an amber oil which was distilled to furnish 25.3 parts of 7-bromoheptyl 2-n-propylphenyl ether, b.p. 140°–160°/0.5-0.2 mm.

b. Ethyl 4-oxo-8[7-(2-n-propylphenoxy)heptyloxy]-4H-1-benzopyran-2-carboxylate

A mixture of 4.84 parts of ethyl 8-hydroxy-4-oxo-4H-1-benzopyran-2-carboxylate, 12.5 parts of 7-bromoheptyl 2-n-propylphenyl ether, 1 part of potassium iodide and 50 parts of anhydrous acetone was refluxed for 76 hours. After filtration the organic layer was concentrated and chromatographed over silica gel. Elution with benzene/chloroform (1:1) furnished 8.9 parts of ethyl 4-oxo-8-[7-(2-n-propylphenoxy)heptyloxy]-4H-1-benzopyran-2-carboxylate as a gum.

c. 4-Oxo-8-[7-(2-n-propylphenoxy)heptyloxy]-4H-1-benzopyran-2-carboxylic acid.

A solution of 6.72 parts of sodium hydrogen carbonate in 130 parts of water was added to a refluxing solution of 9.63 parts of ethyl 4-oxo-8-[7-(2-n-propylphenoxy)heptyloxy]4H-1-benzopyran-2-carboxylate in 200 parts of ethanol. More water was added to effect a clear solution which was refluxed for 2 hours. Acidification by concentrated hydrochloric acid, of the cooled filtrate furnished 4-oxo-8-[7-(2-n-propylphenoxy) heptyloxy]-4H-1-benzopyran-2-carboxylic acid as a brown oil. The oil was triturated between water and petrol (40°–60°) and crystallisation occurred at the interface to yield 3.4 parts of the purified acid. A solution of the acid in the minimum amount of ethanol was poured into a large volume of water and after 24 hours 2.7 parts of 4-oxo-8-[7-(2-n-propylphenoxy)heptyloxy]-4H-1-benzopyran-2-carboxylic acid hydrate were obtained as colourless needles mp 58°–51°.

Analysis: Found: C, 68.7; H, 6.9; $C_{26}H_{30}O_6 \cdot H_2O$ requires: C, 68.5; H, 7.0%.

d. Sodium 4-oxo-8-[7-(2-n-propylphenoxy)heptyloxy]-4H-1-benzopyran-2-carboxylate An equivalent part of 4-oxo-8-[7-(2-n-propylphenoxy)heptyloxy]-4H-1-benzopyran-2-carboxylic acid and an equivalent part of sodium hydrogen carbonate were dissolved, with heating, in 30 parts of distilled water and the corresponding sodium salt crystallised from the cooled filtrate.

Analysis: Found: C, 64.2; H, 6.5; $C_{26}H_{29}NaO_6 \cdot 3/2 H_2O$ requires: C, 64.0; H, 6.6%.

EXAMPLE 14

4-Oxo-7-[7-(2-n-propylphenoxy)heptyloxy]-4H-1-benzopyran-2-carboxylic acid a. Ethyl 4-oxo-7-[7-(2-n-propylphenoxy)heptyloxy]-4H-1-benzopyran-2-carboxylate A mixture of 4.82 parts of ethyl 7-hydroxy-4-oxo-4H-1-benzopyran-2-carboxylate, 12.5 parts of 7-bromoheptyl (2-n-propyl)phenyl ether, 1 part of potassium iodide and 50 parts of anhydrous potassium carbonate were refluxed in 500 parts of anhydrous acetone for 64 hours. The filtrate was concentrated and chromatographed over silica gel to furnish 11.3 parts of a gum which on rechromatography over silica gel afforded 5.0 parts of ethyl 4-oxo-7-[7-(2-n-propylphenoxy)heptyloxy]-4H-1-benzopyran-2-carboxylate which crystallised from petrol (bp. 40°–60°) mp. 55°–57°.

b. 4-Oxo-7-[7-(2-n-propylphenoxy)heptyloxy]-4H-1-benzopyran-2-carboxylic acid

A solution of 2.15 parts of sodium hydrogen carbonate in 40 parts of water was added to a refluxing solution of 3.0 parts of ethyl 4-oxo-7-[7-(2-n-propyl phenoxy)heptyloxy]-4H-1-benzopyran-2-carboxylate in 50 parts of ethanol. More water was added to produce a clear solution which was refluxed for 2 hours. Acidification of the filtrate precipitated the acid as a semi-solid mass which was converted to a fine solid by persistent mechanical disruption of the gum cakes. The solid was filtered off, dried and crystallised from benzene/petrol (bp. 80°–100°) to furnish 2.8 parts of 4-oxo-7-[7-(2-n-propylphenoxy)heptyloxy]-4H-1-benzopyran-2-carboxylic acid as white microcrystals, mp. 149°–150°.

Analysis: Found: C, 71.0; H, 6.95; $C_{26}H_{30}O_6$ requires: C, 71.2; H, 6.85%.

c. Sodium 4-oxo-7-[7-(2-n-propylphenoxy)heptyloxy]-4H-1-benzopyran-2-carboxylate A solution of 0.412 parts of sodium hydrogen carbonate in 20 parts of water was added to a suspension of 2.19 parts of 4-oxo-7-[7-(2-n-propyl phenoxy)heptyloxy]-4H-1-benzopyran-2-carboxylic acid in 30 parts of water and the mixture heated until a clear solution was obtained. The filtrate was freeze dried to furnish 2.19 parts of sodium 4-oxo-7-[7-(2-n-propyl phenoxy)-heptyloxy]-4H-1-benzopyran-2-carboxylate.

Analysis: Found: C, 65.8; H, 6.6; $C_{26}H_{29}NaO_6.H_2O$ requires: C, 65.2; H, 6.5%.

EXAMPLE 15 a. 6-[2-Hydroxy-3-(2-propylphenoxy)propoxy]-4-oxo-4H-1-benzopyran-2-carboxylic acid A mixture of 19.2 parts of 1,2-epoxy-3-(2-propylphenoxy) propane, 23.4 parts of ethyl 6-hydroxy-4-oxo-4H-1-benzopyran-2-carboxylate and 0.1 parts of benzyl trimethylammonium hydroxide in 50 parts of dimethyl formamide was heated under reflux for 3 hours. The solvent was evaporated under reduced pressure and the oil remaining dissolved in ethyl acetate. The solution was washed with dilute sodium hydroxide and water, dried over magnesium sulphate, filtered and evaporated to leave an oil. The oil was dissolved in ethyl alcohol, 20.0 parts of sodium bicarbonate were added, and the mixture was boiled for 2 hours, during which time water was added and the ethyl alcohol allowed to boil off. The aqueous solution was washed with ethyl acetate and acidified with dilute hydrochloric acid to give a brown precipitate which was collected and crystallised twice from ethyl alcohol to yield 10.5 parts of 6-[2-hydroxy-3-(2-propylphenoxy)propoxy]-4-oxo-4H-1-benzopyran-2-carboxylic acid, melting point 164°-166° C.

Analysis: Found: C, 65.9; H, 5.7; $C_{22}H_{22}O_7$ requires: C, 66.3; H, 5.6%.

b. Sodium 6-[2-hydroxy-3-(2-propylphenoxy)-propoxy]-4-oxo-4H-1-benzopyran-2-carboxylate, hemihydrate A mixture of 7.31 parts of 6-[2-hydroxy-3-(2-propylphenoxy)propoxy]-4-oxo-4H-1-benzopyran-2-carboxylic acid and 1.54 parts of sodium bicarbonate in 100 parts of water, was heated to effect solution. The solution was filtered and freeze dried to yield 7.5 parts of sodium 6-[2-hydroxy-3-(2-propylphenoxy)propoxy]-4-oxo-4H-1-benzopyran-2-carboxylate, hemihydrate.

Analysis: Found: C, 51.6; H, 5.2; $C_{22}H_{21}NaO_7.\frac{1}{2}H_2O$ requires: C, 61.5; H, 5.1%.

EXAMPLE 16

(Process (a))

5-[2-Hydroxy-3-(2-propylphenoxy)propoxy]-4-oxo-4H-1-benzopyran-2-carboxylic acid a. 1,2-Epoxy-3-(2-propylphenoxy)propane To a solution of 27.2 parts of 2-propylphenol and 56 parts of 1-chloro-2,3-epoxypropane in 30 parts of ethyl alcohol, heated under reflux, was added a solution of 13.2 parts of potassium hydroxide in 50 parts of ethyl alcohol and 6 parts of water over 15 minutes and the mixture obtained was heated under reflux for a further 2 hours. The mixture was poured into 1,000 parts of water and extracted with ethyl acetate. The organic phase was separated, washed with water, dried over magnesium sulphate, filtered and evaporated to yield a yellow oil. The oil was distilled at the water pump to yield 31.0 parts of 1,2-epoxy-3-(2-propylphenoxy)propane, boiling point 155°-158° at 15 mm.

b. 2-Hydroxy-6-[2-hydroxy-3-(2-propylphenoxy)-propoxy]acetophenone

A solution of 15.2 parts of 2,6-dihydroxyacetophenone 19.2 parts of 1,2-epoxy-3-(2-propylphenoxy)propane and 0.1 parts of benzyl trimethyl-ammonium hydroxide in 50 parts of dimethyl formamide was heated under reflux for 3 hours. The solvent was evaporated under reduced pressure and the oil remaining dissolved in ethyl acetate. The solution was washed three times with dilute sodium hydroxide solution and once with water, dried over magnesium sulphate, filtered and evaporated to leave an oil. The oil was triturated with petroleum ether (bp 40–60°) to yield 25.8 parts of 2-hydroxy-6-[2-hydroxy-3-(2-propylphenoxy)propoxy]acetophenone, as a pale brown solid, melting point indefinite.

c. 5-[2-Hydroxy-3-(2-propylphenoxy)propoxy]-4-oxo-4H-1-benzopyran-2-carboxylic acid A mixture of 25.8 parts of 2-hydroxy-6-[2-hydroxy-3-(2-propylphenoxy)propoxy]acetophenone, 25 parts of diethyl oxalate and 50 parts of dry diethyl ether was added to a stirred solution of sodium ethoxide, prepared from 6.9 parts of sodium and 100 parts of dry ethyl alcohol, and the whole was heated under reflux for 3 hours. The mixture was poured into 1,000 parts of dilute hydrochloric acid and extracted into ethyl acetate. The organic phase was separated and the solvent removed to leave an oil which was dissolved in 250 parts of ethyl alcohol and 1 part of concentrated hydrochloric acid and heated under reflux for 15 minutes. To this solution 20.0 parts of sodium bicarbonate were added and the mixture boiled for 2 hours, during which time water was added and the ethyl alcohol allowed to boil off. The resulting aqueous solution was washed with ethyl acetate and then acidified with dilute hydrochloric acid to give a pale brown precipitate. This solid was collected by filtration and crystallised from ethyl alcohol to yield 11.8 parts of 5-[2-hydroxy-3-(2-propylphenoxy)propoxy]-4-oxo-4H-1-benzopyran 2-carboxylic acid, melting point 168°-170° C.

Analysis: Found: C, 66.5; H, 5.8 $C_{22}H_{22}O_7$ requires: C, 66.3; H, 5.6%.

d. Sodium 5-[2-hydroxy-3-(2-propylphenoxy)-propoxy]-4-oxo-4H-2-carboxylate dihydrate A mixture of 7.55 parts of 5-2-hydroxy-3-(2-propylphenoxy) propoxy-4-oxo-4H-1-benzopyran-2-carboxylic acid and 1.59 parts of sodium bicarbonate in 200 parts of water was heated to effect solution. The solution was filtered while hot and a colourless solid crystallised on cooling to yield 7.7 parts of sodium 5-[2-hydroxy-3-(2-propylphenoxy)propoxy]-4-oxo-4H-1-benzopyran-2-carboxylate, melting point indeterminate.

Analysis: Found: C, 57.5; H, 5.8; $C_{22}H_{21}NaO_7.2H_2O$ requires: C, 57.9; H, 5.5%.

EXAMPLE 17

4-Oxo-7-(3-[2-propylphenoxy]-propoxy)-4H-1-benzopyran-2-carboxylatic acid a. 2-(3-bromopropoxy)propylbenzene A mixture of 200 parts of 2-propylbenzene, 1,500 parts of 1,3-dibromo-propane, 110 parts of anhydrous potassium carbonate, a few crystals of potassium iodide and 2,000 parts of acetone was refluxed for five days and the hot solution filtered. The residue was washed with hot acetone and the combined filtrates evaporated to give an oil which was dissolved in chloroform. The resulting solution was washed with 2H sodium hydroxide solution, water and saturated sodium chloride solution and then dried.

Evaporation of the chloroform and the excess 1,3-dibromopropane under reduced pressure gave 271 parts of 2-(3-bromopropoxy) propylbenzene, b.pt. 149°–151°/6.5 mm.

Analysis: Found: C, 56.3; H, 6.8%; $C_{12}H_{17}BrO$ requires: C, 56.0; H, 6.6%.

b. Ethyl 4-oxo-7-(3-[2-propylphenoxy]-propoxy)-4H-1-benzopyran-2-carboxylate

A mixture of 58.5 parts of ethyl 7-hydroxy-4-oxo-4H-1-benzopyran-2-carboxylate, 64.25 parts of 2-(3-bromopropoxy) propylbenzene, 17.25 parts of anhydrous potassium carbonate and 1000 parts of acetone was refluxed, with stirring, for 2½ days and the hot solution filtered. The residue was washed with hot acetone and the combined filtrates evaporated to give an oil which was dissolved in chloroform. The resulting solution was washed with 1N sodium hydroxide solution and then dried. Evaporation of the chloroform gave an oil which yielded a solid on crystallisation from ethanol. The solid was chromatographed on silica gel, eluting with a 1:1 mixture of ethyl acetate and 40/60 light petroleum ether. Evaporation of the eluent and crystallisation of the resulting residue from ethanol gave 18.4 parts of ethyl 4-oxo-7-(3-[2-propylphenoxy]-propoxy)-4H-1-benzopyran-2-carboxylate, m.pt. 75°–76.5°.

Analysis: Found: C, 70.3; H, 6.6%; $C_{24}H_{26}O_6$ requires: C, 70.2; H, 6.4%.

c. 4-Oxo-7-(3-[2-propylphenoxy]-propoxy)-4H-1-benzopyran-2-carboxylic acid

A solution of 2.05 parts of ethyl 4-oxo-7-(3-[2-propylphenoxy]-propoxy)-4H-1-benzopyran-2-carboxylate and 0.46 parts of sodium bicarbonate in 100 parts of 50% v/v aqueous ethanol was stirred on a steam bath for three hours, then cooled and extracted with ether. The aqueous extract was acidified with excess 2N hydrochloric acid to give a white precipitate which was collected, washed with water and dried. Crystallisation of this solid from acetone gave 1.01 parts of 4-oxo-7-(3-[2-propylphenoxy]propoxy)-4H-1-benzopyran-2-carboxylic acid, m.pt. 168°–171°.

Analysis: Found: C, 69.2; H, 5.7%; $C_{22}H_{22}O_7$ requires: C, 69.1; H, 5.8%.

d. Sodium 4-oxo-7-(3-[2-propylphenoxy]propoxy)-4H-1-benzopyran-2-carboxylate

A mixture of 11.11 parts of 4-oxo-7-(3-[2-propylphenoxy]propoxy)-4H-1-benzopyran-2-carboxylic acid and 2.4 parts of sodium bicarbonate in 200 parts of water was heated to effect solution. The solution was filtered and freeze dried to yield 11.5 parts of sodium 4-oxo-7-(3-[2-propylphenoxy]propoxy)-4H-1-benzopyran-2-carboxylate.

Analysis: Found: C, 62.6; H, 5.3%; $C_{22}H_{21}NaO_6\ 1H_2O$ requires: C, 62.6; H, 5.45%.

EXAMPLE 18

(Process (a))

Ethyl 4-Oxo-7-(3-[2-propylphenoxy]propoxy)-4H-1-benzopyran-2-carboxylate a. 2-hydroxy-4-(3-[2-propylphenoxy]propoxy)acetophenone A mixture of 38 parts of 2,4-dihydroxyacetophenone, 64.25 parts of 2-(3-bromopropoxy)propylbenzene, 17.25 parts of anhydrous potassium carbonate, a few crystals of potassium iodide and 500 parts of acetone was refluxed, with stirring, for 40 hours and the hot solution filtered. The residue was washed with hot acetone and the combined filtrates evaporated to give an oil which was dissolved in chloroform. The chloroform extract was washed with water, dried and evaporated to give a residue which was added to 600 parts of 1N sodium hydroxide solution. The solid produced was filtered, slurried in 200 parts of water and the slurry acidified with 2N hydrochloric acid gave an oil which was extracted into ether. Evaporation of the ether and crystallisation of the resulting residue from 40/60 light petroleum ether gave 38.2 parts of 2-hydroxy-4-(3-[2-propylphenoxy]propoxy)acetophenone, m.pt. 42°–43°.

Analysis: Found: C, 72.9; H, 7.4%; $C_{20}H_{24}O_4$ requires: C, 72.9; H, 7.4%.

b. Ethyl 4-oxo-7-(3-[2-propylphenoxy]propoxy)-4H-1-benzopyran-2-carboxylate

A solution of 0.23 parts of sodium in 10 parts of ethanol was added to a solution of 0.82 parts of 2-hydroxy-4-(3-[2-propylphenoxy]propoxy)acetophenone and 1.46 parts of diethyl oxalate in 15 parts of ether. The reaction mixture was stirred at room temperature for two hours and then poured into a mixture of 10 parts of chloroform, 20 parts of water and 2 parts of concentrated hydrochloric acid. The organic extract was separated, washed with water and dried. Evaporation of the chloroform gave an oil which was refluxed in 20 parts of ethanol containing a drop of concentrated hydrochloric acid for 30 minutes. Evaporation of the solvent gave a solid which crystallised from ethanol to give 0.73 parts of ethyl 4-oxo-7-(3-[2-propylphenoxy]-propoxy)-4H-1-benzopyran-2-carboxylate, m.pt. 73°–75°.

Analysis: Found: C, 69.9; H, 6.4%; $C_{24}H_{26}O_6$ requires: C, 70.2; H, 6.4%.

EXAMPLE 19

(Process (d))

5-(4-oxo-7-[3-{2-propylphenoxy}-propoxy]-4H-1-benzopyran-2-yl) tetrazole a. 4-oxo-7-(3-[2-propylphenoxy]propoxy)-4H-1-benzopyran-2-carboxamide Gaseous ammonia was blubbled through a suspension of 95 parts of ethyl 4-oxo-7-(3-[2-propylphenoxy]-propoxy)-4H-1-benzopyran-2-carboxylate in 1140 parts of ethanol for one hour. The suspension gradually changed in appearance to give a flocculent, yellow solid which was collected and washed with ethanol. Crystallisation of the solid from 1:1 chloroform/ethanol gave 64.2 parts of 4-oxo-7-(3-[2-propylphenoxy]-propoxy)-4H-1-benzopyran-2-carboxamide, m.pt. 210°–213°, (raised to 212°–214° by recrystallisation).

Analysis: Found: C, 69.1; H, 6.1; N, 3.7%; $C_{22}H_{23}NO_5$ requires: C, 69.3; H, 6.0; N, 3.7%.

b. 4-oxo-7-(3-[2-propylphenoxy]-propoxy)-4H-1-benzopyran-2-carbonitrile 46.35 parts of phosphorus oxychloride was added to 750 parts of stirred, ice-cold dimethylformamide to give a solution to which was slowly added 57.15 parts of 4-oxo-7-(3-[2-propylphenoxy]propoxy)-4H-1-benzopyran-2-carboxamide. The reaction mixture was stirred at room temperature for 24 hours and the solution obtained was poured into 3,500 parts of ice water. The solid formed was collected, washed with water and crystallised from ethanol to give 42.2 parts of 4-oxo-7-(3-[2-propylphenoxy]-propoxy)-4H-1-benzopyran-2- carbonitrile, m.pt. 85°–86° (raised to 86°–88° on further purification).

Analysis: Found: C, 72.7; H, 6.1; N, 3.9%; $C_{22}H_{21}NO_4$ requires: C, 72.7; H, 5.8; N, 3.9%.

c. 5-(4-oxo-7-[3-{2-propylphenoxy}-propoxy]-4H-1-benzopyran -2-yl)tetrazole

A mixture of 38.1 parts of 4-oxo-7-(3-[2-propylphenoxy]-propoxy)-4H-1-benzopyran-2-carbonitrile, 7.52 parts of sodium azide, 6.16 parts of ammonium chloride and 5,000 parts of dimethylformamide was stirred at 80° C for 15 hours. The reaction mixture was cooled and 2,000 parts of 2N hydrochloric acid were added to give a yellow solid which was collected. This product was dissolved in hot 3% sodium bicarbonate solution and the hot solution filtered and then cooled. The solid obtained was collected, washed with water and slurried with 500 parts of 2N hydrochloric acid. The resulting solid was collected, washed with water, dried and crystallised from acetone to give 18.4 parts of 5-(4-oxo-7-[3- 2-propylphenoxy -propoxy]-4H-1-benzopyran-2-yl)-tetrazole m.pt. 191°–193°.

Analysis: Found: C, 65.0; H, 5.7; N, 13.8%; $C_{22}H_{22}N_4O_4$ requires: C, 65.0; H, 5.4; N, 13.8%.

d. 5-(4-oxo-7-[3-{2-propylphenoxy}propoxy]-4H-1-benzopyran-2-yl)tetrazole, sodium salt To 250 parts of water was added 16.069 parts of 5-(4-oxo-7-[3-{2-propylphenoxy} propoxy]-4H-1-benzopyran-2-yl)tetrazole and 3.322 parts of sodium bicarbonate and the mixture was heated to effect solution. The hot solution was filtered and 50 parts of ethanol were added. On cooling, a thick amorphous mass obtained which was collected and dried over phosphorus pentoxide to yield 16.8 parts of 5-(4-oxo-7-[3- 2-propylphenoxy propoxy]-4H-1-benzopyran-2-yl)tetrazole, sodium salt.

EXAMPLE 20

(Process (c))

4-Oxo-7-(3-[2-propylphenoxy]propoxy)-4H-1-benzopyran-2-carboxylic acid

A suspension of 1.0 parts of 4-oxo-7-(3-[2-propylphenoxy]propoxy)-4H-1-benzopyran-2-carboxamide in 10 parts of dioxane and 10 parts of 10% v/v sulphuric acid was heated on a steam can for eight hours. The solid obtained on cooling was collected, washed with water and crystallised from acetone to give 0.75 parts of 4-oxo-7-(3-[2-propylphenoxy]propoxy)-4H-1-benzopyran-2-carboxylic acid, m.pt. 164°–166°.

This product was shown by spectral means to be the same as that prepared in Example 18 (c).

EXAMPLE 21

(Process (c))

4-Oxo-7-(3-[2-propylphenoxy]propoxy)-4H-1-benzopyran-2-carboxylic acid

A suspension of 1.0 parts of 4-Oxo-7-(3-[2-propylphenoxy]propoxy)-4H-1-benzopyran-2-carbonitrile in 50 parts of dioxane and 50 parts of 38% v/v sulphuric acid was heated on a steam can for eighteen hours. The solid obtained on cooling was collected, washed with water and crystallised from acetone to give 0.09 parts of 4-oxo-7-(3-[2-propylphenoxy]propoxy)-4H-1-benzopyran-2-carboxylic acid, m.pt. 161°–163°.

This product was shown by spectral means to be the same as that prepared in Example 18(c).

EXAMPLE 22

(Process (a))

8-Ethyl-4-oxo-7-(3-[2-propylphenoxy]propoxy)-4H-1-benzopyran-2-carboxylic acid a. 2-Hydroxy-6-(3-2-propylpheoxy]propoxy)acetophenone A stirred mixture of 76 parts of 2,6-dihydroxyacetophenone, 128.5 parts of 2-(3-bromopropoxy)-propylbenzene, 38 parts of anhydrous potassium carbonate, a few crystals of potassium iodide and 700 parts of acetone was refluxed for 40 hours and the hot solution filtered. The residue was washed with hot acetone and the combined filtrates evaporated to give an oil which was dissolved in chloroform. The resulting solution was washed with 2N sodium hydroxide solution and water and then dried.

Evaporation of the chloroform gave a residue which crystallised from ethanol (with carbon treatment) to give 104.7 parts of 2-hydroxy-6-(3-[propylphenoxy]-propoxy)acetophenone, m.pt.61°–64° (raised to 65°–66° by recrystallisation).

Analysis: Found: C; 72.7; H, 7.3%; $C_{20}H_{24}O_4$ requires: C, 73.2; H, 7.3%.

b. 2-Ethyl-3-(3-[2-propylphenoxy]propoxy)phenol 174.1 parts of zinc wool, 13.05 parts of mercuric chloride, 8.7 parts of concentrated hydrochloric acid and 216 parts of water were shaken together for 15 minutes. The aqueous layer was decanted, the amalgamated zinc was covered with 130.5 parts of water, 174.1 parts of concentrated hydrochloric acid, 290 parts of dioxan and 94 parts of 2-hydroxy-6-(3-[2-propylphenoxy]propoxy)acetophenone and the mixture refluxed for 16 hours. The reaction mixture was cooled, and insoluble material removed by filtration. The organic layer was separated and the aqueous layer was extracted with chloroform. The combined organic extracts were washed with water and saturated sodium chloride solution and dried. Evaporation of the chloroform gave 84.8 parts of 2-ethyl-3-(3-[2-propylphenoxyl]propoxy)phenol, b.pt. 208°–210°/1.8 mm.

Analysis: Found: C, 76.0; H, 8.6%; $C_{20}H_{26}O_3$ requires: C, 76.4; H, 8.3%.

c. Dimethyl 2-ethyl-3-(3-[2-propylphenoxy]propoxy)phenoxyfumarate

A mixture of 73.9 parts of 2-ethyl-3-(3-[2-propylphenoxy]propoxy)phenol, 35.0 parts of acetylene dicarboxylic acid, dimethyl ester and 4 parts of benzyl trimethyl ammonium hydroxide was warmed, with stirring, to 70° when an exothermic reaction occurred. The reaction mixture was maintained at 100°–120° for a further fifteen minutes, cooled, and 1000 parts of 1N sodium hydroxide solution was added. The mixture was extracted with chloroform and the chloroform extract washed with water and saturated sodium chloride solution and dried. Evaporation of the chloroform gave an oil which on trituration with 40/60 petrol gave a solid that crystallised from methanol to give 43.4 parts of dimethyl 2-ethyl-3-(3-[2-propylphenoxy]propoxy)-phenoxy fumarate, m.pt. 63.5°–66° (raised to 71°–72.5° by recrystallisation).

Analysis: Found: C, 68.6; H, 7.3%; $C_{26}H_{32}O_7$ requires: C, 68.4; H, 7.0%.

d. 2-ethyl-3-(3-[2-propylphehoxy]propoxy)phenoxyfumaric acid

A solution of 42.0 parts of dimethyl 2-ethyl-3-(3-[2-propylphenoxy]propoxy)phenoxyfumaric acid and 7.36 parts of sodium hydroxide in 50% v/v aqueous methanol was refluxed for four hours. The reaction mixture was cooled, acidified with excess 2N hydrochloric acid and extracted with chloroform. Evaporation of the chloroform and trituration of the residue with 40/60 light petroleum ether gave an oily solid. This solid was dissolved in hot chloroform and addition of 40/60 light petroleum ether to the solution gave 33.8 parts of 2-ethyl-3-(3-[2-propylphenoxy]propoxy)-phenoxyfumaric acid, m.pt. 104°–105°.

Spectral Confirmation

Molecular weight = 428 (Mass Spectroscopy); $C_{24}H_{28}O_7$ requires 428.

e. 8-Ethyl-4-oxo-7-(3-[2-propylphenoxy]propoxy)-4H-1-benzopyran-2-carboxylic acid A mixture of 1.07 parts of 2-ethyl-3-(3-[2-propylphenoxy]propoxy)phenoxyfumaric acid and 1 part of concentrated sulphuric acid was shaken at room temperature for seventeen hours, then 25 parts of water were added. The resulting solution was made basic by addition of excess sodium carbonate, then re-acidified with 2N hydrochloric acid and extracted with ethyl acetate. Evaporation of the ethyl acetate under reduced pressure gave an oil which on trituration with acetone gave 0.674 parts of 8-ethyl-4-oxo-7-(3-[2-propylphenoxyl]propoxy)-4H-1-benzopyran-2-carboxylic acid, m.pt. 198°–199°.

Spectral Confirmation

Molecular weight = 410 (Mass Spectroscopy); $C_{24}H_{25}O_6$ requires 410.

EXAMPLE 23

(Process (a))

5-(3-[2-Acetyl-3-3-hydroxyphenoxy]-2-hydroxypropoxy)-4-oxo-4H-1-benzopyran-2-carboxylic acid a. Ethyl 5-(3-[2-acetyl-3-hydroxyphenoxy]-2-hydroxypropoxy)-4-oxo-4H-1-benzopyran-2-carboxylate A solution of 69.0 parts of sodium in 1000 parts of ethanol was added to a mixture of 360.3 parts of 1.3-bis-(2-acetyl-3-hydroxyphenoxy)propan-2-ol, 146.1 parts of diethyl oxalate and 250 parts of ethanol. The reaction mixture was refluxed for five hours, then poured into a stirred mixture of 700 parts of chloroform, 3,000 parts of water and 285 parts of concentrated hydrochloric acid. The solid obtained was removed by filtration, the chloroform phase of the filtrate separated and the aqueous phase extracted with chloroform. The combined chloroform extracts were washed with water and concentrated to give a solid which was removed by filtration. Evaporation of the chloroform from the filtrate give a residue which, after fractional crystallisation from ethanol, gave 36.0 parts of slightly impure ethyl 5-(3-[2-acetyl-3-hydroxyphenoxy]-2-hydroxypropoxy)-4-oxo-4H-1-benzopyran-2-carboxylate, m.pt. 145°–148°.

b. Sodium 5-(3-[2-acetyl-3-hydroxyphenoxy]-2-hydroxypropoxy)-4-oxo-4H-1-benzopyran-2-carboxylate 32.0 parts of ethyl 5-(3-[2-acetyl-3-hydroxyphenoxy]-2-hydroxypropoxy)-4-oxo-4H-1-benzopyran-2-carboxylate were refluxed with a solution of 6.08 parts of sodium bicarbonate in 200 parts of water for eighteen hours. The solution was filtered hot and cooled. The solid obtained was collected by filtration and crystallised from water containing a small quantity of ethanol to give 9.2 parts of sodium 5-(3-[2-acetyl-3-hydroxyphenoxy]-2-hydroxypropoxy)-4-oxo-4H-1-benzopyran-2-carboxylate, m.pt. 178°–180°.

Analysis:

Found: C, 55.10; H, 4.34%; $C_{21}H_{17}NaO_9H_2O$ requires: C, 55.50; H, 4.21%.

EXAMPLE 24

(Process (a))

Ethyl 5-(3-[4-oxo-4H-1-benzopyran-5-yloxy]-2-hydroxypropoxy)-4-oxo-4H-1-benzopyran-2-carboxylate A solution of 7.36 parts of sodium in 111 parts of ethanol was added to a suspension of 14.4 parts of 1,3-bis(2-acetyl-3-hydroxyphenoxy)propan-2-ol in 23.68 parts of ethyl formate and 63.3 parts of ethanol and the reaction mixture stirred at room temperature for 3 days. 46.8 parts of diethyl oxal te were then added and the reaction mixture stirred from a further 16 hours. The suspension was poured into a stirred mixture of 370 parts of chloroform and 250 parts of 2N hydrochloric acid and the organic extract separated, washed with water and dried.

Evaporation of the chloroform gave an oil which was refluxed for 1 hour in 316 parts of ethanol containing 4 parts of concentrated hydrochloric acid. A solid was obtained by cooling the solution. On frictional crystallisation (twice) of this product for ethanol, a yellow solid was obtained by evaporation of the mother liquors of the second crystallisation. Chromotagraphy of this solid on silica gel, eluting with 1:1 toluene/acetic acid, gave a solid which crystallised from ethanol to give 0.138 parts of ethyl 5-(3-[4-oxo-4H-1-benzopyran-5-yloxy]-2-hydroxypropoxy)-4-oxo-4H-1-benzopyran-2-carboxylate, m.pt. 155°–159°.

Spectral Confirmation

The n.m.r. and mass spectral data were in agreement with the indicated structure.

Molecular weight = 452 (Mass spectroscopy); $C_{24}H_{20}O_9$ requires = 452.

EXAMPLE 25

(Process (e) and (f))

Ethyl 5-(3-[4-oxo-4H-1-benzopyran-5-yloxy]-2-hydroxypropoxy)-4-oxo-4H-1-benzopyran-2-carboxylate a. Ethyl 5-(3-[2- 3-dimethylaminoacryloyl 3-hydroxyphenoxy]-2-hydroxypropoxy)-4-oxo-4H-1-benzopyran-2-carboxylate A mixture of 0.884 parts of ethyl 5-(3-[2-acetyl-3-hydroxyphenoxy]-2-hydroxypropoxy)-4-oxo-4H-1-benzopyran-2-carboxylate and 0.235 parts of N,N-dimethylformamidedimethylacetal was stirred in 43 parts of xylene at 120°–130° for 3 hours whilst the methanol produced was removed simultaneously by fractional distillation. Overnight cooling of the resulting solution gave a solid which was collected and crystallised from ethanol to give 0.3362 parts of ethyl 5-(3-[2-{3-dimethylaminoacryloyl}-3-hydroxyphenoxy]-2-hydroxypropoxy)-4-oxo-4H-1-benzopyran-2-carboxylate, m.pt.159°–165°.

b. Ethyl 5-(3-[4-oxo-4H-1-benzopyran-5-yloxy]-2-hydroxypropoxy)-4-oxo-4H-1-benzopyran-2-carboxylate 0.200 parts of ethyl 5-(3-[2-{3-dimethylaminoacryloyl}-3-hydroxyphenoxy]-2-hydroxypropoxy)-4-oxo-4H-1-benzopyran-2-carboxylate were refluxed for 16 hours in 15.8 parts of ethanol containing 1 part of concentrated hydrochloric acid. The solution was poured into a stirred mixture of 10 parts of water and 73 parts of chloroform and the organic extract separated, and washed with 5% sodium bicarbonate solution and water. Evaporation of the chloroform gave a residue which was chromatographed on silica gel, eluting with 1:1 chloroform/ethyl acetate. The product obtained from chromatography was crystallised from ethanol to give 0.027 parts of ethyl 5-(3-[4-oxo-4H-1-benzopyran-5-yloxy]-2-hydroxypropoxy)-4-oxo-4H-1-benzopyran-2-carboxylate, m.pt. 154°–158°.

Spectral Confirmation

The n.m.r. and mass spectral data were in agreement with the indicated structure.

molecular weight = 452 (Mass spectroscopy);

$C_{24}H_{20}O_9$ requires = 452.

EXAMPLE A

The procedure set out below is used to assess the effectiveness of a compound in antagonizing SRS-A. The test makes use of the agonist (contractile) effect of SRS-A on isolated guinea-pig ileum.

A satisfactory preparation of SRS-A can be obtained from egg albumen sensitised guinea-pigs. Three weeks after sensitisation, the lungs from such guinea-pigs are removed, perfused free of blood, and chopped. Samples of washed, chopped lung are then challenged with egg albumen (antigen) solution. The supernatants collected 15 minutes after addition of antigen contain histamine and SRS-A and can be used, in the presence of an antihistamine, to induce effects due to SRS-A.

An isolated section of the terminal portion of a guinea-pig ileum is suspended in Tyrode solution, which contains atropine sulphate $10^{-6}M(700\mu g/litre)$ and mepyramine maleate $10^{-6}M$ (400μg/litre). Antropine sulphate is included in reduce the spontaneous activity of the ileum preparation and to exclude the effects of possible cholinergic agents. Mepyramine maleate is included to exclude the effects of histamine. The composition of the Tyrode solution in g/l distilled water is NaCl 8.0, KCl 0.2, $CaCl_2$ 0.2, $MgCl_2$ 0.1, $NaHCO_3$ 1.0, $NaH_2PO_4 2H_2O$ 0.05 and dextrose 1.0. A 2 ml organ bath is preferred economy of SRS-A, the tension on the tissue should be about 600 mg and the bathing temperature 37° C.

A dose of unpurified SRS-A is selected which produces similar repetitive submiximal contractions of the ileum. Each contraction is recorded for 90 seconds when the tissue is washed to allow relaxation. Five minutes is allowed between doses of SRS-A.

The compound under test is added to the organ bath 30 seconds before a dose of SRS-A. A range of concentrations of the compound is chosen to give a log concentration/inhibitory response graph. From this graph, the concentration of compound which would inhibit the ileum concentration to SRS-A by 50% ($IC_{50}$) is determined.

We claim:

1. A pharmaceutical composition for antoganizing the slow reacting substance of anaphylaxis which comprises a compound of the formula:

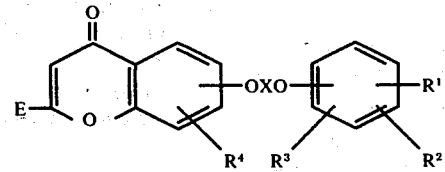

wherein

X is straight chain alkylene containing 3 to 7 carbon atoms and is unsubstituted or is substituted by hydroxy, $R^1$, $R^2$ and $R^3$ are the same or different and are hydrogen, hydroxy, methoxy, benzyloxy, acetyl, acetylamino, allyl or propyl, provided that at least one of $R^1$, $R^2$ and $R^3$ are other than hydrogen or hydroxy, $R^4$ is hydrogen, allyl or propyl, and E is a carboxy group or pharmaceutically acceptable salt thereof, as active ingredient, in an amount effective to antagonize the slow reacting substance of anaphylaxis, in admixture with a pharmaceutically acceptable adjuvant, diluent or carrier.

* * * * *